(12) United States Patent
Zhang et al.

(10) Patent No.: US 8,981,162 B2
(45) Date of Patent: Mar. 17, 2015

(54) METHOD FOR PREPARING FLUORINE-CONTAINING VINYL ETHER

(75) Inventors: Ming Zhang, Fushun County Zigong (CN); Xucang Yang, Fushun County Zigong (CN); Xiaofeng Peng, Fushun County Zigong (CN)

(73) Assignee: Zhonghao Chenguang Research Institute of Chemical Industry Company Limited, Fushun County Zigong (CN)

( * ) Notice: Subject to any disclaimer, the term of this patent is extended or adjusted under 35 U.S.C. 154(b) by 0 days.

(21) Appl. No.: 14/359,059

(22) PCT Filed: Aug. 15, 2012

(86) PCT No.: PCT/CN2012/080145
§ 371 (c)(1),
(2), (4) Date: May 16, 2014

(87) PCT Pub. No.: WO2013/071780
PCT Pub. Date: May 23, 2013

(65) Prior Publication Data
US 2014/0330046 A1     Nov. 6, 2014

(30) Foreign Application Priority Data
Nov. 16, 2011   (CN) .......................... 2011 1 0362820

(51) Int. Cl.
*C07C 41/18* (2006.01)

(52) U.S. Cl.
CPC ..................................... *C07C 41/18* (2013.01)
USPC ........................................ 568/683; 568/685

(58) Field of Classification Search
CPC ............................... C07C 41/18; C07C 41/24
USPC .................................................. 568/683, 685
See application file for complete search history.

(56) References Cited

U.S. PATENT DOCUMENTS

| 3,250,808 A | 5/1966 | Milian, Jr. et al. |
| 5,777,179 A | 7/1998 | Liang et al. |

FOREIGN PATENT DOCUMENTS

| CN | 101213168 A | 7/2008 |
| CN | 101215225 A | 7/2008 |
| CN | 101659602 A | 3/2010 |
| CN | 101817728 A | 9/2010 |
| CN | 102516039 A | 6/2012 |

*Primary Examiner* — Sikarl Witherspoon
(74) *Attorney, Agent, or Firm* — Knobbe Martens Olson & Bear LLP

(57) ABSTRACT

Provided is a method for preparing fluorine-containing vinyl ether. The method comprises: carrying out hydrolytic neutralization on a small molecular weight byproduct which is produced in the process of preparing perfluoropolyether or a perfluorinated surfactant by photooxidation of fluorine-containing olefin; and obtaining fluorine-containing vinyl ether by drying and cracking. The byproduct produced in the process of preparing perfluoropolyether or the perfluorinated surfactant is utilized, thereby solving the emission problem of industrial wastes, reducing environment pollution, and generating available fluorine-containing vinyl ether.

13 Claims, No Drawings

METHOD FOR PREPARING FLUORINE-CONTAINING VINYL ETHER

CROSS-REFERENCE TO RELATED APPLICATIONS

This application is the U.S. National Phase under 35. U.S.C. §371 of International Application PCT/CN2012/080145, filed Aug. 15, 2012, which claims priority to Chinese Patent Application No. 201110362820.1, filed Nov. 16, 2011. The disclosures of the above-described applications are hereby incorporated by reference in their entirety. The International Application was published under PCT Article 21(2) in a language other than English.

TECHNICAL FIELD

The present invention relates to a method for preparing fluorine-containing vinyl ether, more specifically, to a method for preparing fluorine-containing vinyl ether from a byproduct which is produced in the process of preparing perfluoropolyether or a perfluorinated surfactant by photooxidation of fluorine-containing olefin. The present invention relates to polymer chemistry field.

BACKGROUND ART

Fluorine-containing vinyl ether is a widely used polymer compound. Through copolymerization with other monomers for preparing fluoropolymers, it can prepare such materials as fluororesin, fluororubber, etc. that have special functions and are used under special conditions.

Fluorine-containing vinyl ether can be prepared from fluorine-containing acyl fluoride having a structure unit of

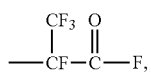

such as

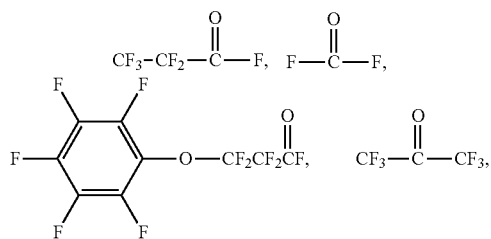

etc. A lot of patents and literatures reported this preparation method, of which a literature indicated that the basic principle for preparing corresponding ether from fluorine-containing acyl fluoride is that perfluorinated acyl fluoride is at first reacted with salt-forming agent to generate perfluorinated carboxylate. Take sodium carbonate as an example, the salt-forming process thereof is:

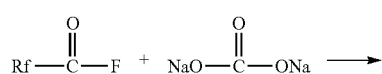

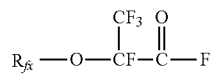

Then the temperature is increased, the carboxylate is decomposed into $CO_2$ and NaF, so as to prepare corresponding ether.

Currently, there are three main methods for preparing fluorine-containing vinyl ether:

First method: U.S. Pat. Nos. 3,321,532 and 3,291,843 disclose that in a nickel tube reactor, a nitrogen flow carries fluorine-containing acyl fluoride vapor to pass through a pipe loaded with metallic oxides ($SiO_2$, CaO, ZnO, etc.), to prepare perfluorinated vinyl ether by cracking at a high temperature larger than 300° C. The maximum yield of the perfluorinated vinyl ether in the example reaches 95%, the preparation method thereof is simple and has a high yield.

Second method: U.S. Pat. Nos. 4,772,756, 4,554,112 and CN1520393A disclose that fluorine-containing acyl fluoride forms salt with $K_2CO_3$ or $NaCO_3$ in the solvent, then cracks at the temperature of about 120° C. in the solvent, finally the perfluorinated vinyl ether which cracks from the solvent is obtained by evaporation. Such method controls the perfluorinated vinyl by the addition of N,N-dimethyl formamide to generate tetra-fluorinated ethyl ether containing hydrogen. The yield of these methods is further improved, and the yield can reach up to 96%.

Third method: U.S. Pat. No. 3,114,778 and CN101659602 disclose that acyl fluoride is neutralized with alkali to form fluorine-containing carboxylate, then dried and cracked at about 220° C. The perfluorinated vinyl ether prepared by such method has the lowest level of hydrogen-containing ether (which refers to fluorine-containing ether in which —O—CF=CF$_2$ group is changed into —O—CFHCF$_3$ group).

Generally, fluorine-containing acyl fluoride represented by general formula of

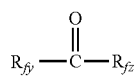

can be prepared by the addition reaction of fluorine-containing carbonyl compound $$R_{fy}-\overset{O}{\underset{\|}{C}}-R_{fz}$$

with hexafluoropropylene oxide in the presence of catalysis and solvent, wherein $R_{fy}$ and $R_{fz}$ may be —F or fluorine-containing alkyl. For example, U.S. Pat. No. 4,035,388 discloses a method for preparing fluorine-containing acyl fluoride by reacting fluorine-containing carbonyl compound with hexafluoropropylene oxide in dimethylamino difluorine phosphine and diglyme; U.S. Pat. No. 3,274,239 describes that fluorine-containing carbonyl compound reacts with hexafluoropropylene oxide in diethanol dimethyl ether with cesium fluoride as the catalyst to prepare fluorine-containing acyl fluoride; U.S. Pat. No. 3,250,808 provides a detailed description on self-aggregation of hexafluoropropylene oxide to prepare

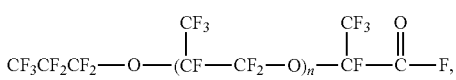

meanwhile it also describes that some other fluorine-containing acyl fluoride are reacted with hexafluoropropylene oxide to generate corresponding

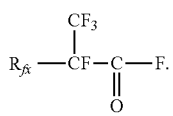

Thereby, fluorine-containing acyl fluoride having a structure unit of

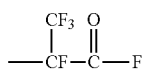

can be obtained.

SUMMARY OF THE INVENTION

The object of present invention is to provide a method for preparing fluorine-containing vinyl ether from a byproduct which is produced in the process of preparing perfluoropolyether or a perfluorinated surfactant by photooxidation of fluorine-containing olefin via a novel approach.

In order to achieve the object of the present invention, the present invention provides a method for preparing fluorine-containing vinyl ether, comprising carrying out hydrolytic neutralization on a small molecular weight byproduct which is produced in the process of preparing perfluoropolyether or a perfluorinated surfactant by photooxidation of fluorine-containing olefin; and obtaining fluorine-containing vinyl ether by drying and cracking. The fluorine-containing olefin may be monomers such as perfluoropropylene, tetrafluoroethylene, trifluorobromoethylene, etc., especially perfluoropropylene.

The byproducts used for preparing fluorine-containing vinyl ether mainly involve the light components with a relatively smaller molecular weight, the light components mainly refer to the compounds having a molecular weight smaller than 400, and specifically refer to acyl fluoride having a structure unit of —O—$CF_2(CF_3)$CFO.

The main source of fluorine-containing acyl fluoride in the present invention is a large quantity of light component byproducts with relatively smaller molecular weight which are produced in the process of preparing perfluoropolyether or a perfluorinated surfactant by photooxidation of perfluoropropylene or tetrafluoroethylene, wherein such light components has a molecular weight smaller than 400. And these fluorine-containing acyl fluoride mainly include perfluorinated propionyl fluorine, perfluorinated acetyl fluoride, fluorophosgene, $CF_3CF_2CF_2OCF_2(CF_3)$CFO, $CF_3OCF_2(CF_3)$CFO, $CF_3CF_2OCF_2(CF_3)$CFO and so on, mainly comprising $CF_3CF_2CF_2OCF_2(CF_3)$CFO, $CF_3OCF_2(CF_3)$CFO, $CF_3CF_2OCF_2(CF_3)$CFO, which can be detected by using methanol esterification method.

The acetyl fluoride which can be used for preparing fluorine-containing vinyl ether must have a structure unit of —O—$CF_2(CF_3)$CFO. If perfluoropropylene is used as the raw material in the process of preparing perfluoropolyether or a perfluorinated surfactant by photooxidation, one of the important byproducts is 2-perfluorinated propoxy propionyl fluoride, moreover, the content thereof are varied greatly depending on different photooxidation reaction conditions, and the content can reach up to 5%. Such byproduct can be used for preparing perfluorinated n-propyl vinyl ether. In addition, other byproducts further comprises 2-perfluorinated methoxyl propionyl fluoride, 2-perfluorinated ethyoxyl propionyl fluoride, both having a content between 1% and 6%, which can be respectively used for preparing perfluorinated methyl vinyl ether and perfluorinated ethyl vinyl ether. It is not suitable for these byproducts to prepare fluorinated ether oil due to too small molecular weight; and it is also not suitable for them to prepare fluorine-containing surfactant due to relatively shorter molecular chain. It certainly can not be treated simply for waste, even be discharged, which will not only increase production cost, but also result in severe environmental pollution.

2-perfluorinated propoxy propionyl fluoride, 2-perfluorinated methoxyl propionyl fluoride, 2-perfluorinated ethyoxyl propionyl fluoride are important raw materials for preparing perfluorinated n-propyl vinyl ether, perfluorinated methyl vinyl ether and perfluorinated ethyl vinyl ether, thus the best method is to collect them for preparing fluorine-containing vinyl ether. The researchers of the present invention consider three different processes by which fluorine-containing vinyl ether can be prepared from fluorine-containing propionyl fluoride in the mixed gases.

The first process is to collect various fractions of fluorine-containing propionyl fluoride by direct purification of these acyl fluorides. However, this method is relatively complicated to operate due to the materials involved with very high toxicity, thus the processing device must have good seal, and it should be placed in a good ventilation environment.

The second process is to first hydrolyze all these acyl fluorides into acids which are less toxic and easy for control, purify the acids, and finally react with alkali metal hydroxide to neutral, and then are cracked after drying to prepare perfluorinated n-propyl ether, which has a high requirement for corrosion resistance of equipment.

The third process is to dry and crack them after directly neutralizing these materials, to prepare fluorine-containing vinyl ether mixed with impurities, and then purify the fluorine-containing vinyl ether, which is relatively simple and does not have a high requirement for equipment. Thus the present invention adopts this process to prepare various fluorine-containing vinyl ethers.

The hydrolytic neutralization of the present invention is to convert these acyl fluorides in the byproducts into fluorine-containing carboxylic acids. Specifically, firstly a storage tank filled with the products prepared by photooxidation is heated with warm water, wherein the heating temperature can be controlled at 60~70° C.; the product evaporated from the storage tank is fed into a reactor which is filled with alkalic metal lye and equipped with a condensation backflow device, the reactor has stirring function, and the stirring speed is controlled at 500~1000 revolution/min. The materials for the hydrolytic reaction reactor are preferably lined with a fluorine-containing resin, or use hastelloy.

The hydrolytic neutralization process is relatively easy, but the output of heat during the reaction is large, cooling should be concerned. Typically, the temperature is controlled below 100° C., preferably below 50° C., for example 30~50° C. When the temperature of hydrolytic neutralization product is lowered to room temperature, the product can be released, then the hydrolytic neutralization product is dried to give solid salt (which is fluorine-containing carboxylate as a solid).

When the hydrolytic neutralization is performed, the alkalic metal lye particularly KOH or NaOH is added, the pH value of neutralized fluorine-containing carboxylate solution is preferably controlled at 8~10. If the pH value is too low, the acidity is high, such that there may be incomplete neutralization; if the pH value is too high, more hydroxide is remained, which is detrimental to later preparation of fluorine-containing vinyl ether by cracking.

It is necessary to dry the fluorine-containing carboxylate after hydrolytic neutralization according to the present invention so as to remove the water therein. Particularly the less content of water is better, and in the case where the drying environment is not lower than 100° C., it is possible to dry it at both normal pressure and reduced pressure.

The fluorine-containing carboxylate obtained by drying in the present invention is placed into a cracking device. It is preferred that the cracking device has a stirrer. The stirring speed is set at 50~100 revolution/min, so that the materials can be evenly heated. The cracking temperature is controlled at not lower than 180° C., preferably at 190~220° C. If the temperature is low, the cracking speed is slow; if the temperature is too high, a large amount of byproducts will be generated. The cracking time is 20~30 hours.

The finally obtained product is collected by a coldtrap. The product collected by the coldtrap is transferred to a rectifying tower, according to the different boiling points of various fluorine-containing vinyl ethers, various fluorine-containing vinyl ethers are collected by rectification.

The method for preparing fluorine-containing vinyl ether according to the present invention utilizes the byproduct which is produced in the process of preparing perfluoropolyether or perfluorinated surfactant, thereby not only solving the emission problem of industrial wastes, reducing environment pollution, but also turning the waste materials into things of value and generating available fluorine-containing vinyl ether. Such method is simple and can be easily operated, so as to provide a reliable way of advantageously managing byproduct pollution after a large scale production of perfluoropolyether or perfluorinated surfactant.

EXAMPLE

The following examples are used for illustrating the present invention, but not used for limiting the scope of the present invention.

Example 1

An irradiation device, viz. ultra-violet lamp (the wavelength is 250 nm~400 nm) having a power of 250 W is installed on a pressure-tolerant steel reactor which has a jacket and a volume of 20 L, the reactor is provided with a backflow device at −70° C. 20 Kg of perfluorinated propylene (HFP) which is precooled to −45° C. is added into the precooled reactor; a measured mixed gas comprising 20 L/h of oxygen ($O_2$) (standard state) and 2.5 L/h of perfluorinated methyl vinyl ether (PMVE) are introduced into the bottom of the reactor, the reaction phase is kept at about −45° C. for 8 hours; then the ultra-violet lamp is turned off to stop the reaction; the freezing recovery of HFP is stopped, and the reaction materials after the recovery of HFP are pushed into an intermediate tank for storage.

10.00 Kg of materials evaporated from the reactor with warm water at 65° C., in which the content of each material respectively is: 3.5% of perfluorinated propionyl fluoride, 2.8% of perfluorinated acetyl fluoride, 2.0% of fluorophosgene, 25.5% of $CF_3CF_2CF_2OCF_2(CF_3)CFO$, 20.4% of $CF_3OCF_2(CF_3)CFO$, 16.8% of $CF_3CF_2OCF_2(CF_3)CFO$, 2.9% of perfluorinated propylene and 26.1% of other impurities, are added into 30 L of hydrolysis reactor with a stirring device for hydrolytic neutralization, wherein the reactor is lined with fluorine-containing resin and filled with 20 wt % KOH, the temperature is controlled at 48° C., the stirring speed is controlled at 800 revolution/min, 20 wt % KOH is supplemented appropriately and the pH value of the solution is adjusted to 9. The neutralized materials are cooled to the room temperature, and discharged out for drying to obtain 8.6 Kg of dried fluorine-containing carboxylate.

The completely dried fluorine-containing carboxylate is loaded into 20 L of stainless steel cracking reactor with a stirring device, the stirring speed is set at 100 revolution/min, and the reactor is heated to 220° C. to crack for 20 hours, and then collected by a coldtrap at −30° C. to obtain 2.13 Kg of products. After measurements, the products comprises 32% of perfluorinated n-propyl vinyl ether, 21.7% of perfluorinated methyl vinyl ether, 17.4% of perfluorinated ethyl vinyl ether and other components which are a small amount of hydrogen-containing ether of various corresponding vinyl ether (the molecular formular is Rf—OCFH—$CF_3$, Rf can be $CF_3CF_2CF_2$—, $CF_3$—, $CF_3CF_2$—), a little $CO_2$ and a little cracking byproduct such as fluorine-containing acyl fluorides, etc. Finally, perfluorinated n-propyl vinyl ether, perfluorinated methyl vinyl ether and perfluorinated ethyl vinyl ether are collected by rectification in a rectifying tower.

Example 2

An irradiation device, viz. ultra-violet lamp (the wavelength is 250 nm~400 nm) having a power of 250 W is installed on a pressure-tolerant steel reactor which has a jacket and a volume of 20 L, the reactor is provided with a backflow device at −70° C.; 20 Kg of perfluorinated propylene (HFP) which is precooled to −45° C. is added into the precooled reactor; a measured mixed gas comprising 20 L/h of oxygen ($O_2$) (standard state) and 1.5 L/h of chlorotrifluor ethylene (CTFE) are introduced into the bottom of the reactor, the reaction phase is kept at about −45° C. for 8 hours; then the ultra-violet lamp is turned off to stop the reaction; the freezing recovery of HFP is stopped, the reaction materials after the recovery of HFP are pushed into an intermediate tank for storage.

10.00 Kg of materials evaporated from the reactor with warm water at 70° C., in which the content of each material respectively is: 2.9% of perfluorinated propionyl fluoride, 3.7% of perfluorinated acetyl fluoride, 1.6% of fluorophosgene, 20.3% of $CF_3CF_2CF_2OCF_2(CF_3)CFO$, 26.9% of $CF_3OCF_2(CF_3)CFO$, 23.0% of $CF_3CF_2OCF_2(CF_3)CFO$, 2.6% of perfluorinated propylene and 19.0% of other impurities, are added into 30 L of hydrolysis boiler with a stirring device for hydrolytic neutralization, wherein the reactor is lined with fluorine-containing resin and filled with 20 wt % KOH, the temperature is controlled at 60° C., the stirring speed is controlled at 500 revolution/min, 20 wt % KOH is supplemented appropriately and the pH value of the solution is adjusted to 10. The neutralized materials are cooled to the room temperature, and discharged out for drying to obtain 9.1 Kg of dried fluorine-containing carboxylate.

The completely dried fluorine-containing carboxylate is loaded into 20 L of stainless steel cracking reactor with a stirring device, the stirring speed is set at 80 revolution/min, and the reactor is heated to 190° C. to crack for 20 hours, and then collected by a coldtrap at −30° C. to obtain 2.13 Kg of products. After measurements, the products comprises 23.0% of perfluorinated n-propyl vinyl ether, 0.5% of perfluorinated methyl vinyl ether, 25.8% of perfluorinated ethyl vinyl ether, other components which are a small amount of hydrogen-containing ether of various corresponding vinyl ether (the molecular formular is Rf—OCFH—$CF_3$, Rf can be $CF_3CF_2CF_2$—, $CF_3$—, $CF_3CF_2$—), a little $CO_2$ and a little cracking byproduct such as fluorine-containing acyl fluorides, etc. Finally, perfluorinated n-propyl vinyl ether, perfluorinated methyl vinyl ether and perfluorinated ethyl vinyl ether are collected by rectification in a rectifying tower.

Example 3

An irradiation device, viz. ultra-violet lamp (the wavelength is 250 nm~400 nm) having a power of 250 W is installed on a pressure-tolerant steel reactor which has a jacket and a volume of 20 L, the reactor is provided with a backflow device at −70° C.; 5 L perfluorinated dimethyl ether which is precooled to −45° C. is added into the precooled reactor; a measured mixed gas comprising 20 L/h of oxygen ($O_2$) (standard state) and 2 Kg/h of hexafluoropropylene are introduced into the bottom of the reactor, the reaction phase is kept at about −45 ° C. for 8 hours; then the ultra-violet lamp is turned off to stop the reaction; the freezing recovery of HFP is stopped, the reaction materials after the recovery of HFP are pushed into an intermediate tank for storage.

10.00 Kg of materials evaporated from the reactor using the warm water at 60° C., in which the content of each material respectively is: 2.8% of perfluorinated propionyl fluoride, 2.4% of perfluorinated acetyl fluoride, 1.9% of fluorophosgene, 29.8% of $CF_3CF_2CF_2OCF_2(CF_3)CFO$, 27.6% of $CF_3OCF_2(CF_3)CFO$, 13.3% of $CF_3CF_2OCF_2(CF_3)CFO$, 1.2% of perfluorinated propylene and 21.0% of other impurities, are added into 30 L hydrolysis reactor with a stirring device for hydrolytic neutralization, wherein the reactor is lined with fluorine-containing resin and filled with 20 wt % KOH, the temperature is controlled at 30° C., the stirring speed is controlled at 500 revolution/min, 20 wt % KOH is supplemented appropriately and the pH value of the solution is adjusted to 8. The neutralized materials are cooled to the room temperature, and discharged out for drying to obtain 9.3 Kg of dried fluorine-containing carboxylate.

The completely dried fluorine-containing carboxylate is loaded into 20 L of stainless steel cracking reactor with a stirring device, the stirring speed is set at 50 revolution/min, and the reactor is heated to 200° C. to crack for 20 hours, and then collected by a coldtrap at −30° C. to obtain 2.54 Kg of products. After measurements, the product comprises 34% of perfluorinated n-propyl vinyl ether, 29.0% of perfluorinated methyl vinyl ether, 14.7% of perfluorinated ethyl vinyl ether and other components which are a small amount of hydrogen-containing ether of various corresponding vinyl ether (the molecular formular is Rf—OCFH—$CF_3$, Rf can be $CF_3CF_2$—, $CF_3$—, $CF_3CF_2$—), a little $CO_2$ and a little cracking byproduct such as fluorine-containing acyl fluorides, etc. Finally, perfluorinated n-propyl vinyl ether, perfluorinated methyl vinyl ether and perfluorinated ethyl vinyl ether are collected by rectification in a rectifying tower.

Although the present invention has been described in detail by general description and specific embodiments in the context, it is obvious to a person skilled in the art to make some modifications or improvements thereto based on the present invention. Therefore, all these amendments or improvements without departing from the spirit of the present invention are covered within the scope claimed by the present invention.

Industrial Applicability

The present invention provides a method for preparing fluorine-containing vinyl ether, comprising carrying out hydrolytic neutralization on a small molecular weight byproduct which is produced in the process of preparing perfluoropolyether or a perfluorinated surfactant by photooxidation of fluorine-containing olefin; and drying and cracking to prepare fluorine-containing vinyl ether. The method for preparing fluorine-containing vinyl ether according to the present invention utilizes the byproduct which is produced in the process of preparing perfluoropolyether or perfluorinated surfactant, thereby not only solving the emission problem of industrial wastes, reducing environment pollution, but also turning the waste materials into things of value and generating available fluorine-containing vinyl ether, thus the present invention possesses industrial applicability.

What is claimed is:

1. A method for preparing fluorine-containing vinyl ether, comprising carrying out hydrolytic neutralization on a small molecular weight byproduct which is produced in the process of preparing perfluoropolyether or a perfluorinated surfactant by photooxidation of fluorine-containing olefin; and obtaining fluorine-containing vinyl ether by drying and cracking.

2. The method of claim 1, characterized in that, the small molecular weight byproduct is a compound with a molecular weight smaller than 400.

3. The method of claim 1, characterized in that, the small molecular weight byproduct contains acyl fluoride having a structure unit of —O—$CF_2(CF_3)$CFO.

4. The method of claim 3, characterized in that, the acyl fluoride comprises: $CF_3CF_2CF_2OCF_2(CF_3)CFO$, $CF_3OCF_2(CF_3)CFO$ or $CF_3CF_2OCF_2(CF_3)CFO$.

5. The method of claim 4, characterized in that, the small molecular weight byproduct is obtained by heating the product of preparing perfluoropolyether or a perfluorinated surfactant by photooxidation at 60~70 ° C. and evaporation.

6. The method of claim 1, characterized in that, the hydrolytic neutralization is carried out in alkali metal lye and the pH is controlled at pH 8~10.

7. The method of claim 6, characterized in that, the hydrolytic neutralization is carried out under stirring, and the stirring speed is controlled at 500~1000 revolutions/min.

8. The method of claim 1, characterized in that, the temperature for hydrolytic neutralization is controlled below 100° C.

9. The method of claim 1, characterized in that, the cracking temperature is not lower than 180° C., and the cracking time is 20~30 hours.

10. The method of claim 1, characterized in that, the fluorine-containing olefin monomer adopted in the process of preparing perfluoropolyether or a perfluorinated surfactant by photooxidation is perfluoropropylene, tetrafluoroethylene or trifluorobromoethylene.

11. The method of claim 1, characterized in that the temperature for hydrolytic neutralization is controlled at 30~50°C.

12. The method of claim 1, characterized in that the cracking temperature is from 190~220°C. and the cracking time is 20~30 hours.

13. The method of claim 1, characterized in that the fluorine-containing olefin monomer adopted in the process of preparing perfluoropolyether or a perfluorinated surfactant by photooxidation is perfluoropropylene.

* * * * *